United States Patent [19]

Hertl et al.

[11] 4,105,498

[45] Aug. 8, 1978

[54] ANEROBIC SPECIMEN TRANSPORT SYSTEM

[75] Inventors: William Hertl; William S. Ramsey, both of Corning, N.Y.

[73] Assignee: Corning Glass Works, Corning, N.Y.

[21] Appl. No.: 798,659

[22] Filed: May 19, 1977

[51] Int. Cl.$^2$ ............................................. C12K 1/08
[52] U.S. Cl. ...................................... 195/59; 195/126
[58] Field of Search ................. 195/126, 107, 127, 59

[56] References Cited

U.S. PATENT DOCUMENTS 4,030,978  6/1977  Abramson ............................ 195/127

OTHER PUBLICATIONS

Merck Index, 8th Ed., p. 372 (1968).

*Primary Examiner*—Alvin E. Tanenholtz
*Attorney, Agent, or Firm*—William E. Maycock; Clinton S. Janes, Jr.; Clarence R. Patty, Jr.

[57] ABSTRACT

A deoxygenated, inert, oil-like fluid having an oxygen activity coefficient less than that of water may be used to provide anaerobic conditions for the transport and/or storage of anaerobic specimens.

10 Claims, No Drawings

ANEROBIC SPECIMEN TRANSPORT SYSTEM

BACKGROUND OF THE INVENTION

1. Field

This disclosure is concerned generally with the transport of an anaerobic microbe specimen from a place of collection to a place of examination. More specifically, the disclosure is concerned with the use of a medium which is especially useful for the transport of a microbial sample under strictly anaerobic and substantially non-growing conditions.

2. Prior Art

The anaerobic bacteria are a class of microorganisms the growth and survival of which requires an environment substantially free of oxygen. In many cases (e.g. for purposes of identifying or studying the anaerobes), it is necessary to transport a sample of anaerobic bacteria from a collection point to an examination point under conditions which exclude substantially all contact with air or oxygen. For example, since it is known that certain anaerobic bacteria are responsible for a variety of infections (surgical wound, uro-genital, pulmonary, etc.), it is often necessary to collect, transport, and culture specimens under anaerobic conditions to determine the cause and treatment for a given infection. Since even traces of oxygen may be toxic to anaerobic bacteria, it is clear that the collection, transportation, storage and culture of any specimen (clinical or otherwise) should be done under suitable anaerobic conditions.

The ideal bacteria transport system would allow the survival of all types of microbes (aerobic and anaerobic) without allowing the multiplication of any. Although a variety of different transport systems consisting of swabs in tubed media is commercially available, none is fully suitable for the transport and/or storage of anaerobic specimens. See, for example, Ederer, G. M. et al., "Evaluation of Bacteriological Transport Systems", *Amer. J. of Med. Tech.* 41, 299–306 (1975). Although sterile mineral oil has been used to cover the surface of certain cultures and thereby merely exclude contamination from atmospheric oxygen, we are unaware of the use of any such fluid to not only exclude oxygen but also enhance anaerobicity.

It has recently been suggested that specimens destined for anaerobic study should be transported under anaerobic conditions without the use of nutrient media or chemical reducing agents. See, for example, *Anaerobe Laboratory Manual*, Ed. L. V. Holdeman et al., Virginia Polytechnic Institute, 1973, wherein the collection and transport of fluid specimens in syringes and the transport of solid specimens via swabs in tubes containing $O_2$-free $CO_2$ are recommended.

We have now developed an anaerobic specimen transport system which permits the transport and/or storage of anaerobic specimens in a non-nutrient anaerobic milieu in which the activity of any contaminating oxygen from the specimen itself is lessened without the use of chemical reducing agents. Details of our anaerobic specimen transport system and methods of using it are described in detail herein.

SUMMARY OF THE INVENTION

Our anaerobic specimen transport system comprises an anaerobic specimen in contact with a water-immiscible, substantially non-nutritive, sterile, inert, deoxygenated oil-like fluid having an oxygen activity coefficient less than that of water and, preferably, a specific gravity less than that of the specimen. In other preferred embodiments the oil-like fluid is a silicone oil such as dimethyl silicone and anaerobicity of a specimen is maintained and enhanced by contacting at least a portion of the specimen with the fluid.

SPECIFIC EMBODIMENTS

Although our anaerobic specimen transport system is illustrated below with a specific silicone oil (dimethyl silicone), it should be appreciated that other similar media may be used as long as a given medium meets the following requirements:

(1) It should be deoxygenated or degassed and have an oxygen activity coefficient less than that of the specimen to serve as an oxygen sink or getter with respect to any oxygen that might be inadvertently introduced into the system via the specimen itself, the specimen collection process, or from other sources;

(2) It should be substantially water-immiscible;

(3) It should be substantially non-nutritive, sterile, non-toxic, and inert with respect to the sample to be transported; and (4) It should have a fluidity (preferably a viscosity of about 1 to 30,000 centistokes or cs) such that at least a portion of the anaerobic specimen can be immersed in the medium. Depending on the specific gravity of the media vis-a-vis the specimen, at least a portion of the specimen may be retained immersed using mechanical means (e.g. a plunger) or by gravity. In preferred embodiments, the specific gravity of the fluid is less than the sample so that the specimen can settle in the fluid. For tissue specimens, this generally means a specific gravity of less than water or about 1.0.

Examples of oil-like fluids which meet the above requirements include silicone oils such as dimethyl silicone oils and phenylmethyl silicone oils, fluid fluorocarbons, etc.

As shown below, oxygen dissolved in a representative medium, dimethyl silicone oil, has a low activity coefficient so that large quantities of gases dissolve in the oil. When degassed silicone is in contact with a specimen (e.g. an exudate, etc.), any gaseous oxygen in the specimen will equilibrate with the oil until the oxygen activities are equal in each phase. This has the desirable effect of reducing both the concentration and activity of oxygen in the specimen and thus allowing the survival of strictly anaerobic bacteria. Since the silicone oil is also non-nutritive, the anaerobes are not only preserved, but they will not multiply.

Our system can now be illustrated with a typical silicone fluid (dimethyl silicone) which meets all of the above requirements and represents an ideal and preferred medium for the present invention.

It has been found that dimethyl silicone oil dissolves about 26 cc of $O_2$/100 ml. Using an oxygen sensitive (measuring) electrode, we found that the oxygen activity in water (solubility about 3 cc $O_2$/100 ml) equilibrated with air was the same as that of silicone oil equilibrated with air, which, based on physical principles had been expected. The activities of oxygen in both liquids were also identical when the liquids were equilibrated with pure oxygen.

Since activity is the product of concentration and activity coefficient, and since the maximum dissolved oxygen concentration in silicone oil is approximately 8 times that in water, the activity coefficient of oxygen in silicone oil must be approximately ⅛ that in water. An aqueous and oil phase in contact will reach an equilibrium in which the oxygen activity is the same in each phase. Very importantly (with respect to the present disclosure), if the oil phase is initially free of oxygen, and the aqueous phase (e.g. the specimen medium) contains oxygen, both the concentration and activity of oxygen in the aqueous phase will be substantially lower after equilibrium. The oil thus acts as an $O_2$ sink or $O_2$ getter relative to the specimen, thereby substantially enhancing anaerobicity. For example, when equal volumes of air saturated water and partially deoxygenated silicone oil ($O_2$-free $CO_2$ bubbled through the oil for 1 hour) were placed in contact, the oxygen activity in the water phase was reduced by 70%, and equilibration is attained in a short period of time (minutes). It can be appreciated that the $O_2$ getting effect is enhanced as the ratio of oil to specimen is increased.

EXAMPLE

The strictly anaerobic bacterium *Clostridium innocuum*, ATCC 14501, was tested for ability to survive in the deoxygenated (degassed) silicone oil. A culture was prepared under anaerobic conditions and it was diluted about 1/10 with air saturated nutrient broth to simulate a clinical sample contaminated with air during the sampling (collecting) procedure.

The number of viable bacteria was determined by plating samples on pre-reduced agar and gassed with oxygen-free $CO_2$. Two ml samples were added to each of two 20 ml aliquots of silicone oil which has been degassed by heating to 300° C. on a vacuum rack for 1 hour and stored in a sealed vessel. Similar samples were placed in sterile tubes and exposed to the air. All samples were held at room temperature for 24 hours and the number of viable bacteria were determined. The results, expressed in colony forming units per ml (cfu/ml) are shown below. The dimethyl silicone oil had a viscosity of about 20 cs.

TABLE

| Treatment | cfu/ml (Avg. of Duplicates) |
| --- | --- |
| Original suspension | $5.75 \times 10^4$ |
| Silicone oil for 24 hrs. | $6.84 \times 10^4$ |
| Exposed to air for 24 hrs. | $9.5 \times 10^2$ |

The above results show that the degassed fluid may be used to maintain viability for a strict anaerobe for 24 hours.

Compatability with Clinical Specimens

When the transport system of this disclosure is to be used for clinical specimens, it is important that the medium be compatable therewith. The compatability of the silicone oil with clinical specimens was demonstrated with guinea pig tissues.

Approximately 1 gram samples of kidney, muscle, liver, and mesentery tissues, as well as drops of blood and swabs of intestine contents were placed in 5 ml portions of the oil. All samples sank to the bottom of the tube after submersion with a pipette, consistent with the density of the silicone oil (0.97 g/cc) and density of the tissues (slightly greater than 1 g/cc). Pieces of the tissues were then removed with forceps, placed in a water-based nutrient broth, and briefly mixed with a vortex mixer, which caused the tissues to sink, leaving the silicone oil on the surface of the nutrient broth (density 1.008 g/cc). The oil also quickly separated from globules of blood and from swabs, thus allowing the blood and swab contents to mix with the nutrient broth. The media therefore may be separated from the samples by simple immersion in water-based media, a clear convenience.

Liquid samples containing bacteria and suspended in the medium (oil) may be removed with a pipette and gram stained in the usual manner. The presence of the oil on the slide does not interfere with the staining. Swabs containing bacteria may also be gram stained after immersion in silicone oil if care is taken to roll or rub the swab on the slide to insure areas of aqueous phase on the slide.

It should be pointed out the actual form of the specimen to be transported may vary and it is anticipated that this disclosure includes the use of all forms of specimen (e.g. liquid, semi-soild, solid, etc.). Also, the transport medium may be contained in a variety of containers, the exact configuration being determined by other factors such as cost, convenience, etc.

Although it is intended that the system disclosed herein provides a unique method and material for transport and/or storage of all anaerobic specimens, the system is especially suitable for clinical specimens. For example, deoxygenated or degassed silicone oil may be packaged in a number of different ways to provide for convenient clinical sampling. The transport fluid may be included in a sterile pre-packaged syringe for use in sampling fluids. A tube containing degassed silicone oil with a tight seal and small headspace may be used for solid specimens. Such a tube may be provided with a sterile swab so that the absorbent portion of the swabs just above the transport fluid with a handle protruding through the stopper. After sampling, the absorbent portion would be immersed in the fluid.

It should be stressed that a very important aspect of our system is based on the use of a fluid which acts as an oxygen getter or $O_2$ sink relative to the specimen to be introduced into or placed in contact with the system. This requirement is easily met by using a deoxygenated or degassed medium having a relatively low oxygen activity coefficient. Deoxygenation or degassing can be accomplished by a variety of known means. For example, the fluid-like sample may be simply heated as above or exposed to a stream of $O_2$ free gas such as $N_2$, $CO_2$, etc. Alternatively, chemical means may be used to remove any oxygen as long as there are no detrimental effects (toxicity, etc.). The main requirement is that the oxygen level in the fluid is negative relative to the oxygen level of the specimen to be introduced, thereby resulting in a net movement of oxygen from the specimen (sample) to the transport medium. In very preferred embodiments the medium is substantially deoxygenated (e.g. removal of >99% of the dissolved oxygen).

Since the above disclosure is subject to variations, it should be understood that the above examples are merely illustrative and that the invention disclosed herein should be limited only by the following claims.

We claim:

1. A method of maintaining a specimen of an anaerobic microbe under conditions which are substantially anaerobic and which enhance the anaerobicity of the specimen, the method comprising immersing the specimen in a water-immiscible, inert, substantially non-nutritive, sterile, deoxygenated oil-like fluid having an oxygen activity coefficient less than that of water.

2. The method of claim 1 wherein the specific gravity of the fluid is less than that of the specimen.

3. The method of claim 1 wherein the fluid is a silicone oil.

4. The method of claim 3 wherein the oil is a dimethyl silicone oil.

5. The method of claim 3 wherein the silicone oil has a viscosity ranging from about 1 to about 30,000 centistokes.

6. A composite comprising an anaerobic microbe specimen immersed in a water-immiscible, inert, substantially non-nutritive, deoxygenated oil-like fluid having an oxygen activity coefficient less than that of the specimen and which enhances the anaerobicity of the specimen.

7. The composite of claim 6 wherein the specific gravity of the oil-like fluid is less than that of the specimen.

8. The composite of claim 6 wherein the fluid comprises a silicone oil.

9. The composite of claim 8 wherein the oil comprises a dimethyl silicone oil.

10. The composite of claim 8 wherein the viscosity of the oil ranges from about 1 to about 30,000 centistokes.

* * * * *